(12) United States Patent
Schon et al.

(10) Patent No.: US 9,474,620 B2
(45) Date of Patent: Oct. 25, 2016

(54) TALONAVICULAR JOINT PROSTHESIS AND ITS METHOD OF IMPLANTATION

(76) Inventors: Lew C. Schon, Baltimore, MD (US); Christopher Chiodo, Walpole, MA (US); Brent G. Parks, West Friendship, MD (US); Josh Nadaud, St. Louis, MO (US); Zeynep Busra Dinc, Baltimore, MD (US)

(*) Notice: Subject to any disclaimer, the term of this patent is extended or adjusted under 35 U.S.C. 154(b) by 356 days.

(21) Appl. No.: 13/820,664

(22) PCT Filed: Sep. 4, 2010

(86) PCT No.: PCT/US2010/002429
§ 371 (c)(1),
(2), (4) Date: Aug. 21, 2014

(87) PCT Pub. No.: WO2012/030317
PCT Pub. Date: Mar. 8, 2012

(65) Prior Publication Data
US 2014/0371867 A1 Dec. 18, 2014

(51) Int. Cl.
*A61F 2/42* (2006.01)
*A61B 17/16* (2006.01)
*A61F 2/30* (2006.01)

(52) U.S. Cl.
CPC ......... *A61F 2/4202* (2013.01); *A61B 17/1682* (2013.01); *A61B 17/1615* (2013.01); *A61F 2002/3021* (2013.01); *A61F 2002/30143* (2013.01); *A61F 2002/30182* (2013.01); *A61F 2002/30224* (2013.01); *A61F 2002/30247* (2013.01); *A61F 2002/30263* (2013.01); *A61F 2002/30268* (2013.01); *A61F 2002/30332* (2013.01); *A61F 2002/30354* (2013.01); *A61F 2002/30538* (2013.01); *A61F 2002/30738* (2013.01); *A61F 2002/30878* (2013.01); *A61F 2002/30884* (2013.01); *A61F 2002/30892* (2013.01); *A61F 2002/422* (2013.01); *A61F 2002/4207* (2013.01)

(58) Field of Classification Search
CPC ..................... A61F 2/4202; A61F 2002/4205; A61F 2002/4207; A61F 2002/421; A61F 2002/4212; A61F 2002/4215
See application file for complete search history.

(56) References Cited

U.S. PATENT DOCUMENTS 7,025,790 B2 * 4/2006 Parks ..................... A61B 17/15
623/21.11

FOREIGN PATENT DOCUMENTS

WO    WO 2005032426 A1 *  4/2005  ......... A61F 2/30749

* cited by examiner

*Primary Examiner* — Yashita Sharma
*Assistant Examiner* — Daniel Bissing
(74) *Attorney, Agent, or Firm* — Larry J. Guffey (57) ABSTRACT

A talonavicular joint prosthesis (1) adapted to replace the natural talonavicular joint that exists between a patient's talus and navicular bones, after appropriate surgical preparation of the joint-related portions of these bones so as to create a new joint space to accommodate this prosthesis, includes talar (2) and navicular (4) components. Each of these have inner (8, 28) and outer (6, 26) surfaces whose average separate distance is defined as the component's average thickness. These components inner (8, 28) surfaces are configured to: (a) generally follow the anatomic contour of the original joint surface to which each component is to be attached, and (b) minimize each component's average thickness, consistent with providing sufficient strength and rigidity for the components, so as to require minimum bone resection in the creation of the new prosthesis-accommodating, joint space.

9 Claims, 6 Drawing Sheets

TALONAVICULAR JOINT PROSTHESIS AND ITS METHOD OF IMPLANTATION

CROSS-REFERENCE TO RELATED APPLICATION

This application claims the benefit of PCT Patent Application No. PCT/US2010/002429, filed Sep. 4, 2010 by the present inventors. The teachings of this application are incorporated herein by reference to the extent that they do not conflict with the teaching herein.

BACKGROUND OF THE INVENTION

1. Field of the Invention

This invention relates to surgery and orthopaedic instrumentation. More particularly, this invention relates to a talonavicular joint prosthesis and the surgical procedure and apparatus for its implantation.

2. Description of the Related Art

The talonavicular joint is comprised of the articulation between the talus and navicular bones. For many years, one of the more aggressive methods for treating diseased or injured talonavicular joints was a fusion between the talus and navicular bones. Unfortunately, this method has had significant drawbacks—e.g., hindfoot motion is greatly reduced; limiting the motion in the joint results in greater load distribution in adjacent joints—which can yield further degenerative disease. Other widely used treatments have included orthotics, braces, physical therapy and cortisone shots.

More recently, considerable interest has developed in the use of joint replacement methods and equipment (e.g., an artificial joint, called a prosthesis) to treat diseased or injured joints in the foot and ankle. Such methods entail the degenerative articular surfaces of the joint being removed and replaced with a prosthesis.

Among the joints attempted to be treated by joint replacement methods is the talonavicular joint, see U.S. Pat. No. 3,965,489. The prosthesis disclosed in U.S. Pat. No. 3,965,489 consists of disc-shaped talar and navicular components that have interfacing bearing surfaces with complimentary concave and convex curvatures. On the back sides of these surfaces are tapered ribs which are fitted into slots that are surgically created in the talus and navicular bones to which these components are affixed. This prosthesis involves the surgeon utilizing a dorsal approach to the joint and primarily flat cuts across the joint space. Such a surgical approach and the size of the prosthesis' components results in the resection of an inordinate amount of bone and the compromising of adjoining critical bony and soft tissue structures. This situation has reportedly led to the diminishment over time of the stability of the orientation of the prosthesis' components and the ultimate failure of the prosthesis.

There exists a need for the development of an improved talonavicular joint prosthesis that will better follow the natural anatomic contours of the joint space while preserving critical portions of the distal talus and proximal navicular bone surfaces to which it is affixed.

3. Objects and Advantages

There has been summarized above, rather broadly, the prior art that is related to the present invention in order that the context of the present invention may be better understood and appreciated. In this regard, it is instructive to also consider the objects and advantages of the present invention.

It is an object of the present invention to provide an improved talonavicular joint prosthesis for the replacement of the arthritic, deformed, or degenerated talonavicular joint articulation and thereby eliminate the need for talonavicular joint fusion.

It is another object of the present invention to provide a less invasive surgical method for preparing the joint space and inserting a talonavicular joint prosthesis to allow for the preservation of the critical portions of the distal talus and proximal navicular and the better retention and stable attachment of the joint's essential soft tissue structures.

It is another object of the present invention to provide a talonavicular joint prosthesis and its surgical method of implantation that will yield improved patient healing and a decrease in the failure rate of such devices.

It is a further object of the present invention to provide a talonavicular joint prosthesis and its surgical method of implantation that utilizes a precision cutting tool and fixation jig apparatus to prepare the talonavicular joint for the insertion of the prosthesis, wherein this tool and apparatus allow for minimum bone resection by allowing the surgeon to follow the natural contours of the talonavicular joint so as to preserve the strongest portion of the distal talus and proximal navicular for implantation of the talonavicular prosthesis.

It is an object of the present invention to provide a more mechanically sound talonavicular joint prosthesis which is also more conducive to biologic incorporation into a patient's body.

It is also an object of the present invention to provide a talonavicular joint prosthesis which is more mechanically and biologically compatible with arthroplasty of adjacent joints in the foot and ankle.

It is an object of the present invention to provide a talonavicular joint prosthesis and its surgical method of implantation that utilizes a precision cutting tool and fixation jig apparatus which will allow a surgeon to cut forwards and backwards in the patient's new joint space that is created for the prosthesis.

These and other objects and advantages of the present invention will become readily apparent as the invention is better understood by reference to the accompanying summary, drawings and the detailed description that follows.

SUMMARY OF THE INVENTION

Recognizing the need for the development of an improved talonavicular joint prosthesis and the method for preparation and insertion, the present invention is generally directed to satisfying the needs set forth above.

In accordance with the present invention, a talonavicular joint prosthesis for replacing, after the necessary surgical preparation of the appropriate joint-related portions of the patient's talus and navicular bones, a patient's natural talonavicular includes talar and navicular components. Each of these has an inner and an outer surface and a herein defined average thickness, t, that quantifies the average distance between these component surfaces. Additionally, each component's inner surface is configured to generally follow the anatomic contour of the original joint surface to which each component is to be attached and to also minimize its average thickness, t, consistent with providing sufficient strength and rigidity in the prosthesis' components, so as to yield minimum bone resection in the creation of the new prosthesis-accommodating, joint space.

In accordance with the present invention, a method of replacing the natural talonavicular joint that exists between a patient's talus and navicular bones includes the steps of providing especially-designed talar and navicular components, surgically preparing the joint surfaces of the patient's talus and navicular bones so as to create a new joint space to accommodate these components, and surgically implanting these components. Each of these components has an inner and an outer surface and a herein defined average thickness, t, that quantifies the average distance between these component surfaces. Additionally, each component's inner surface is configured to generally follow the anatomic contour of the original joint surface to which each component is to be attached and to also minimize its average thickness, t, consistent with providing sufficient strength and rigidity in the prosthesis' components, so as to yield minimum bone resection in the creation of the new prosthesis-accommodating, joint space.

Thus, there has been summarized above, rather broadly and understanding that there are other preferred embodiments which have not been summarized above, the present invention in order that the detailed description that follows may be better understood and appreciated. There are, of course, additional features of the invention that will be described hereinafter and which will form the subject matter of the later presented claims to this invention.

DESCRIPTION OF THE PREFERRED EMBODIMENT

Before explaining at least one embodiment of the present invention in detail, it is to be understood that the invention is not limited in its application to the details of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

In the preferred embodiment, the talonavicular joint prosthesis 1 of the present invention includes talar 2 and navicular 4 components. See FIGS. 1A-1B and 2A-2B. These components are designed so as to permit a patient who has such a prosthesis implanted to have normal, physiologic hindfoot motion, including rotation and translation in the rear or hind-part of the foot, i.e., the talonavicular joint prosthesis of the present invention reproduces natural talonavicular joint motion.

Figure 1A:
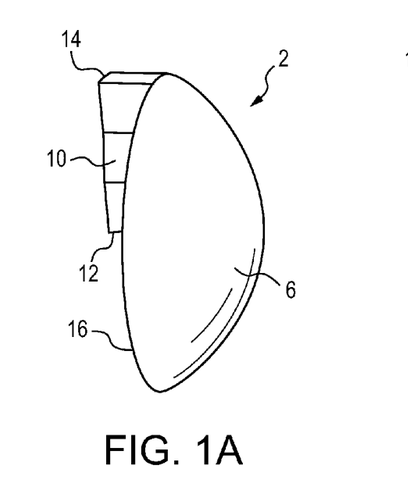
FIGS. 1A and 1B show, respectively, perspective views of the outer and inner surfaces of a talar component of the present invention.

The embodiment of the talar component 2 seen in FIG. 1A has a convex outer (i.e., outer with respect to the talus to which the component is attached) or distal surface 6. This component's inner or proximal surface 8 can be any number of shapes, but it often is shaped so that it is parallel to and concentric to the shape of this component's outer surface so that the distance between these outer and inner surfaces is approximately uniform. Since this distance is ultimately seen to be an important factor in the design of this prosthesis, we quantify it by taking its value at each of the various points or locations on faces of these surfaces, and then averaging these values to define the average thickness, $t_T$, of this talar component.

An advantage of this parallel-concentric surfaces design is that it will ultimately lead to a prosthesis that can have a minimum thickness while also ensuring that the talar component has sufficient strength and rigidity to withstand the stresses that will be placed on this component as it is used in the prosthesis. Achieving such a minimum thickness is important because bone has to be surgically removed from that portion of the talus to which the talar component is to be attached (i.e., the joint-related portion of the talus) so as to provide room in the patient's foot for the prosthesis, and the less bone that has to be removed the better the chances will be for the eventual success of the prosthesis—both in terms of the health of the patient's foot (e.g., reduced bone resorption and inflammation) and lengthening the duration of the prosthesis' effectiveness.

Figure 1B:
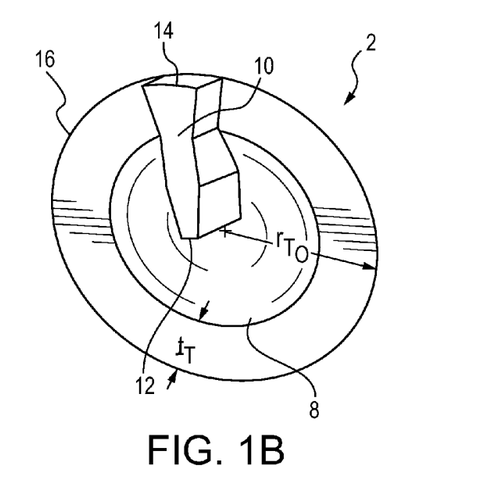

Keeping with this idea of minimizing the amount of bone that must be removed to accommodate the prosthesis leads to a key design criteria for the shaping of the talar component's inner surface—since it can be noted that this minimal bone removal goal can be achieved by configuring the talar component's inner surface 8 so that it generally follows the anatomic contour of the original joint surface to which the talar component is to be attached. This component's outer surface 6 is then shaped so that it is parallel to and concentric to the shape of this component's inner surface 8 so that the distance between these surfaces is approximately uniform and set at a minimal value to provide minimal bone removal.

Despite the relative simplicity of the curvature seen in the components shown in FIGS. 1A-1B and 2A-2B, it should be recognized that the range of curvatures and geometries that can be used on these components are extremely broad and can be quite complex in order to address the wide range of pathologies that can be encountered in patients needing talonavicular joint replacement surgery. For example, curvature in these components' surfaces can be simply quasi-hemispherical or semi-elliptical, or these surfaces can have multiple types of curvature, e.g., they may have portions with distinct and differing curvatures, such as any combination of concavity, convexity or flat portions.

To facilitate fixation of this component to the talus, one or more talar protrusions (e.g., cylinders/rails/plates/beams) 10 extend from its inner surface 8. These may be cylindrical, hemispherical, conical, truncated conical, or trapezoidal in shape. In general, the exact shape of such a protrusion will depend upon the shape, size and weight of the implant component and to the shape of the surgically prepared joint surface (e.g., configured to yield minimum bone resection by following as closely as possible the anatomic contour of the original joint surface) to which the implant is to be affixed. For example, in addition to the complex, trapezoidal shaped protrusion or rail shown in FIGS. 1A-1B, see also the alternative multiple protrusions configurations shown in FIGS. 3A-3D. These protrusions are generally meant to align/protrude perpendicular to the plane of the perimeter 16 of the proximal talar surface. Depending on the direction of this component's insertion into the talus, these protrusions can either be aligned along that direction of insertion or may be aligned slightly obliquely to that direction. When only a single, simple geometry protrusion is used, its point of attachment is usually centrally located on the proximal talar surface. As seen in FIG. 1B, when a single trapezoidal shaped protrusion is used, it has an inner 12 edge that is located proximate the center of the inner talar surface and an outer 14 edge that extends to approximately the perimeter 16 of this component.

Figure 4A:
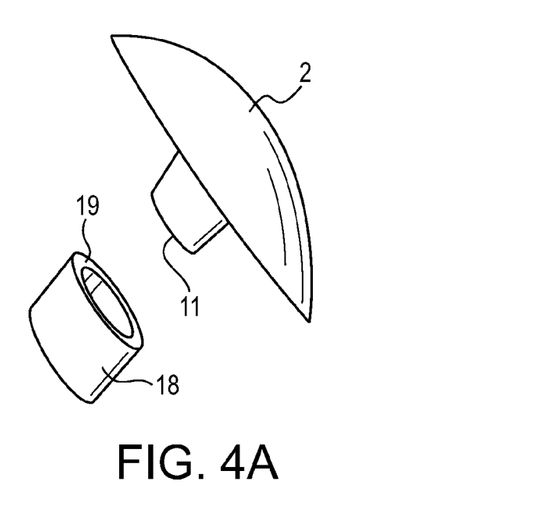
FIGS. 4A-4F show perspective views of the implant receptacles or anchors of the present invention.
Figure 4B:
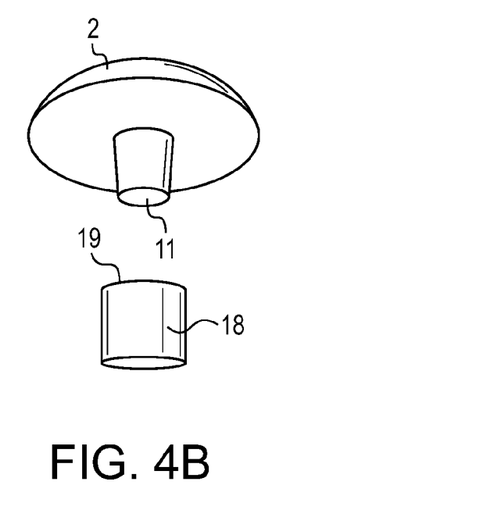
Figure 4C:
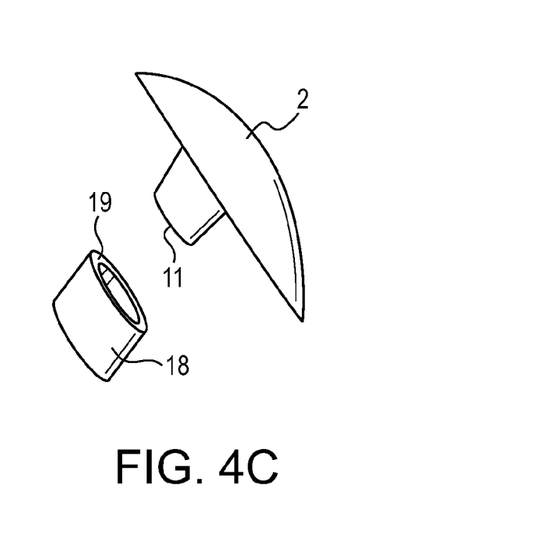
Figure 4D:
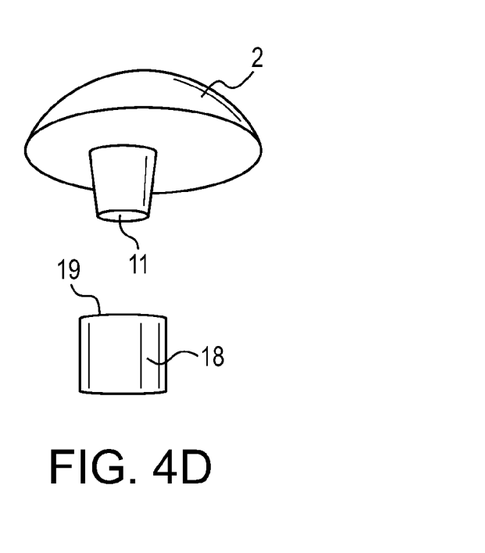

In addition to utilizing the protrusions shown in FIGS. 1-3, the talar component can also be affixed to the talus by alternatively using an especially designed talar implant receptacle or anchor 18. See FIGS. 4A-4D. Such a receptacle is first implanted into the talus. This anchor has an interlocking end 19 that is configured to mate with the suitably interlockingly configured distal end 11 of the talar protrusion/s that extend from the inner surface of the talar component. For example, this interlocking end may employ a locking screw, Morse taper or point to point fit system for adhering the protrusions to the anchor. Also show in FIGS. 4A-4D is some idea of the variety of shapes that the talar component 2 may take. FIGS. 4A-4B show a talar component whose inner or proximal surface is flat and has extending perpendicularly from it a centrally located protrusion. FIGS. 4C-4D show a similar talar component that differs by having its protrusion offset from the the center of the component's flat inner surface.

The talar insert may also serve as a pivot point to allow fine adjustment of the talar component about an "offset" or eccentrically located attachment point that will anchor into the talar insert. As an alternative configuration to the "pivot" point the talar insert may have one or more interlocking grooves or "dovetails" which can interlock with corresponding grooves or "dovetails" on the talar component. These grooves or dovetails would be oriented in a dorsal-plantar direction. There would be multiple grooves on the talar component set at distances which both allow structural integrity while increasing the possible choice of position of the component. The "pivot" point may be a Morse taper interlock mechanism whereby once the correct position has been established the talar component is impacted to lock the taper in place. For the interlocking groove system, once the optimal position is established a "locking mechanism" will be deployed. This locking mechanism can include, but is not limited to wedges, screws, interference fits, etc.

Figure 5A:
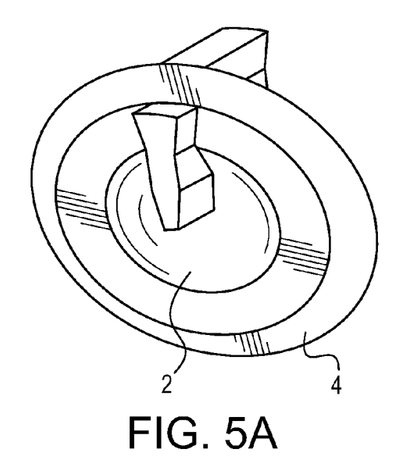
FIGS. 5A-5B show perspective views of the nesting of the present invention's talar and navicular components so as to create a new effective joint surface about which the adjoining talus and navicular bones may move.
Figure 5B:
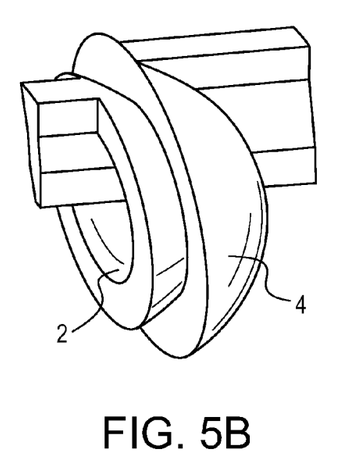

The navicular component 4 of the present invention has a concave outer (i.e., outer with respect to the navicular bone to which the component is attached) surface 26 whose radius, $r_{No}$, is approximately equivalent to or slightly larger than the radius, $r_{To}$, of the talar component's outer surface. This situation allows the talar component's convex outer surface 6 to be adjoined to or nested into the navicular component's concave outer surface 26 so as to create a new effective joint surface about which the adjoining talus and navicular bones will be allowed to move. See FIGS. 5A-5B.

The exact nature of the curvature in these adjoining talar component outer 6 and navicular component outer 26 surfaces can be quite complex in order to address the wide range of pathologies that can be encountered in patients needing talonavicular joint replacement surgery. For example, curvature in these adjoining surfaces can be simply quasi-hemispherical, as shown in FIGS. 1A-1B and 2A-2B, or the surfaces can be semi-elliptical, in which case such elliptical surfaces could be mathematically described in terms of the magnitudes of their minor and major axes rather than just the radius, $r_{To}$ and $r_{No}$, of the components' outer surfaces. Additionally, the surface area of these adjoining surfaces can be comparatively large so as to enable them to include various portions that have distinct and differing curvatures, e.g., any combination of concavity, convexity or flat portions.

Figure 2A:
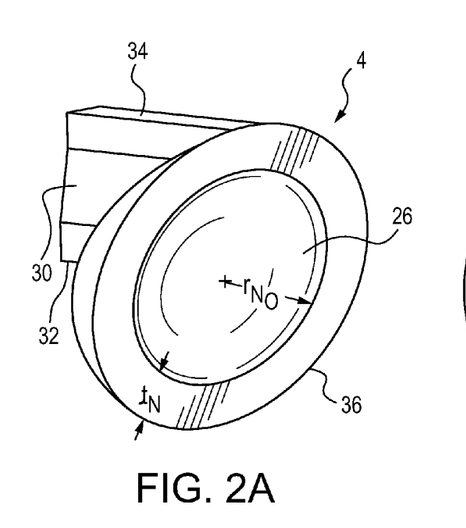
FIGS. 2A and 2B show, respectively, perspective views of the outer and inner surfaces of a navicular component of the present invention.
Figure 2B:
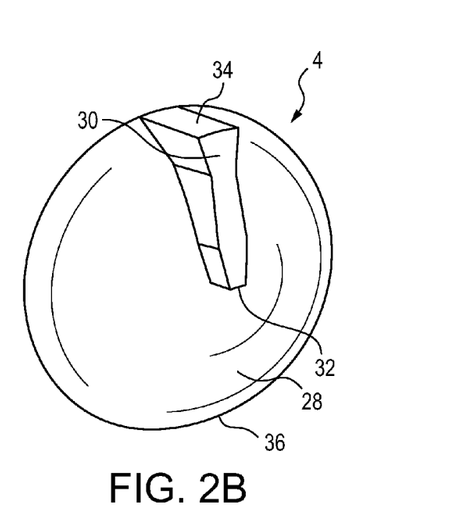
Figure 3A:
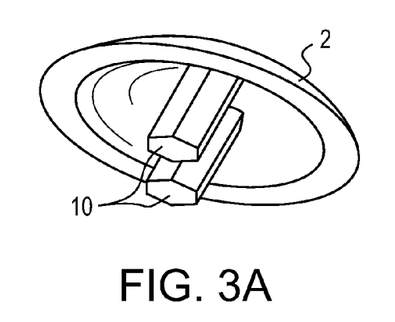
FIGS. 3A-3D show alternative configurations for the protrusions that are used to attach the present invention's talar and navicular components to their adjoining bones.
Figure 3B:
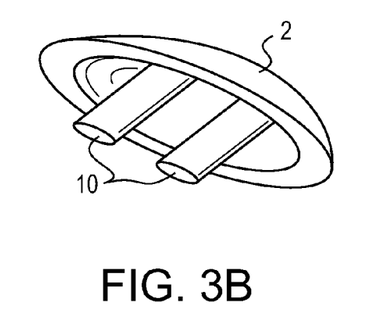
Figure 3C:
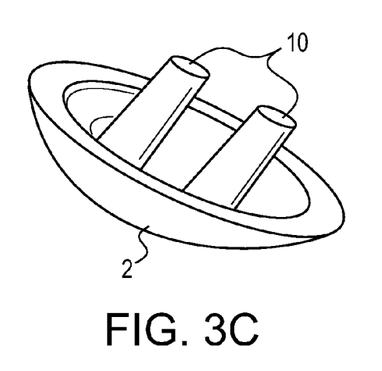
Figure 3D:
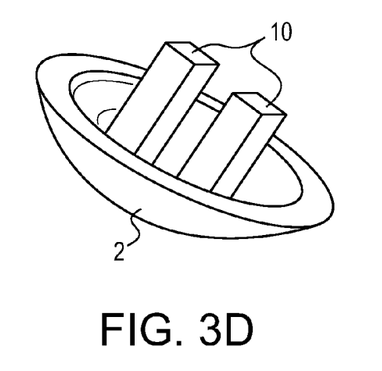

The navicular component's inner or proximal surface 28 is also usually shaped so that it is convex and parallel to and concentric to the shape of this component's concave outer surface so that the distance between these outer and inner surfaces is approximately uniform, i.e., its thickness, $t_N$, is approximately constant. However, a key factor in determining the shape of this component's inner surface 28 is again the requirement that this surface generally follow the anatomic contour of the joint surface to which it is to be attached—thus the portion of the navicular to which this component will be attached will ideally have a concave outer surface. The benefit of this design feature being that it results in minimum bone resection.

While the navicular component shown in FIGS. 2A-2B is symmetrical, it should be recognized that there are instances in which it may be preferable to shape this component so that it is asymmetrical, e.g., so as to avoid the medial side of navicular.

To facilitate fixation of the navicular component to the navicular, one or more navicular protrusions 30 extend from its inner surface 28. Similar to the protrusions used on the talar components, the navicular component's protrusions 30 can take any one of a multitude of shapes and generally align/protrude perpendicular to the plane of the perimeter 36 of the navicular inner surface 28. In general, the exact shape of such a protrusion will depend upon the shape, size and weight of the implant component and to the shape of the surgically prepared joint surface (e.g., configured to yield minimum bone resection by following as closely as possible the anatomic contour of the original joint surface) to which the implant is to be affixed.

Depending on the direction of this component's insertion, these protrusions can either be aligned along that direction of insertion or may be aligned slightly obliquely to that direction. When only a single, simple geometry protrusion is used, its point of attachment is generally centrally located on the proximal talar surface. When a single trapezoidal shaped protrusion is used, it often has an inner 32 edge that is located proximate the center of the inner talar surface and an outer 34 edge that extends to approximately the perimeter 36 of this component.

The navicular component can also be affixed to the navicular by alternatively using an especially designed navicular implant receptacle or anchor 38. See FIGS. 4E-4F. Such a receptacle is first implanted into the navicular. This anchor has an interlocking end 39 that is configured to mate with the suitably interlockingly configured distal end 31 of the navicular protrusion/s that extend from the inner surface of the navicular component. For example, this interlocking end may employ a locking screw, Morse taper or point to point fit system for adhering the protrusions to the anchor.

Figure 4E:
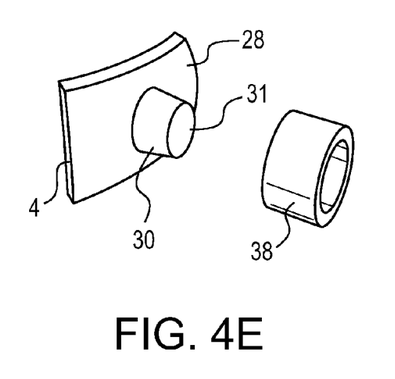
Figure 4F:
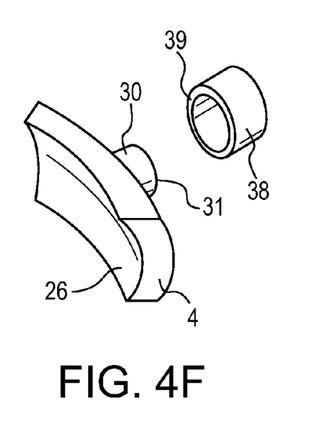

Also shown in FIGS. 4E-4F is some idea of the variety of shapes that a navicular component 4 may take. FIGS. 4E-4F show a navicular component whose inner or proximal surface is convex and has extending perpendicularly from it a centrally located protrusion 30. Meanwhile, the navicular component's outer surface has concave curvature so as to allow it to mate with a talar component having a convex outer surface.

In order a talonavicular joint prosthesis that is biologically compatible with the arthroplasty of adjacent joints in the foot and ankle, any combination of synthetic, naturally occurring, processed or unprocessed biologic materials may be used to supplement the fixation of the present invention's components. This situation allows direct integration of the present invention's biological materials into the bones to which its components are attached.

Figure 6A:
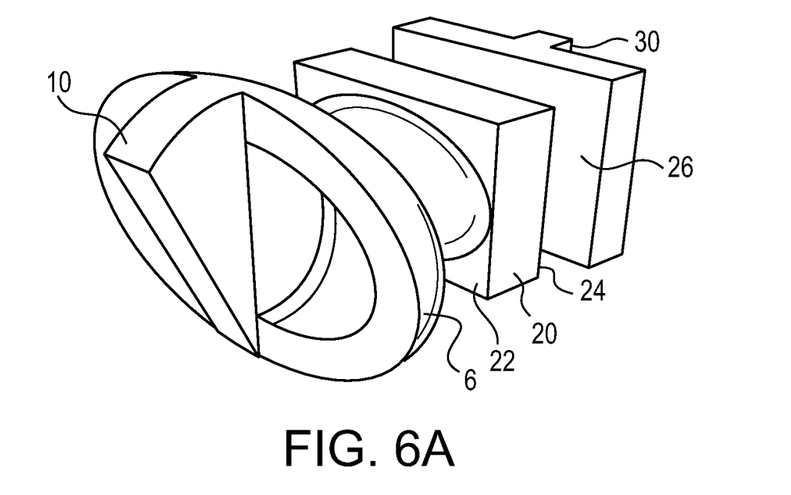
FIGS. 6A-6B show perspective views of a mobile bearing that is suitable for use with the present invention.
Figure 6B:
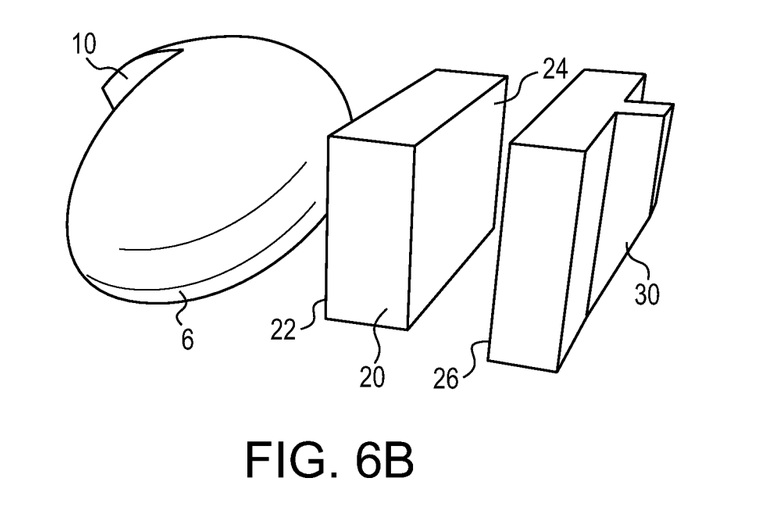

In some instances, the present embodiment can also include a mobile bearing 20 that fits between the outer surfaces of the talar and navicular components. See FIGS. 6A-6B. Such a mobile bearing has proximal 22 and distal 24 surfaces that adjoin the respective outer surfaces of the talar and navicular components. The range of curvatures and geometries that can be used on these surfaces are extremely broad and can be quite complex in order to address the wide range of pathologies that can be encountered in patients needing talonavicular joint replacement surgery. For example, curvature in these surfaces can be simply quasi-hemispherical or semi-elliptical, or these surfaces can have multiple types of curvature, e.g., they may have portions with distinct and differing curvatures, such as any combination of concavity, convexity or flat portions. The example shown in FIGS. 6A-6B is seen to have a proximal surface 22 that has a concave portion that is configured to mate with the convexity in the talar component's outer surface. This mobile bearing also has a flat distal surface 24 that is configured to mate with a navicular component that has a flat outer surface 26.

Preferred materials for the components and/or bearing of the present invention are cobalt chromium, titanium alloy, tantalum and polyethylene. Alternatively, they may be made of a combination of any synthetic, naturally occurring, or preserved, processed or unprocessed biologic materials.

Using the components of the present invention, there are many different ways to surgically approach and create a talonavicular joint space. Each of these may impact on the final design of this prosthesis' talar and navicular components.

Figure 7:
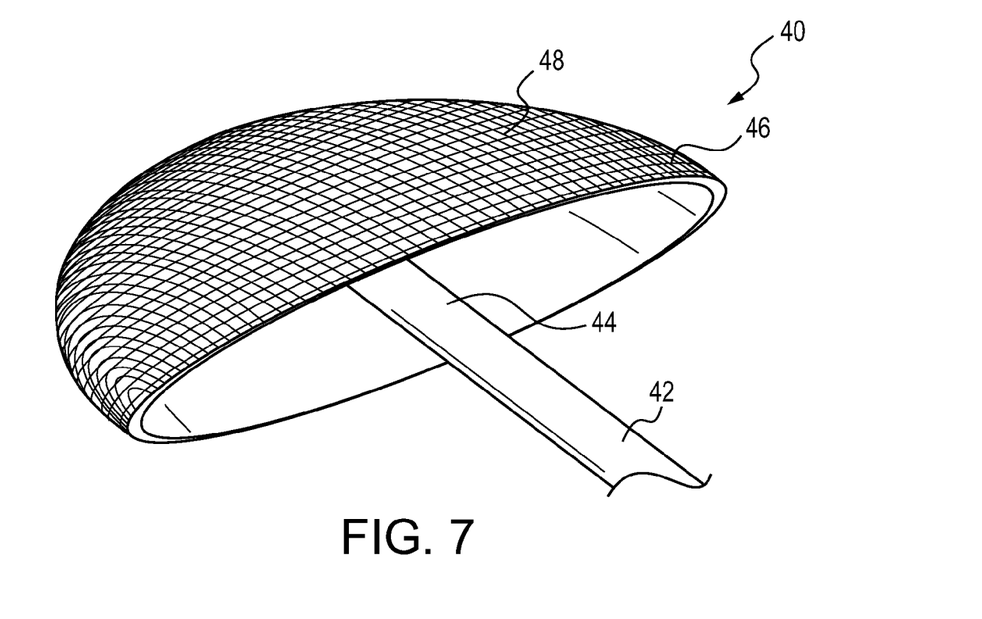
FIG. 7 shows a perspective view of a cutting tool for use in preparing a patient's talus and navicular bones to accommodate said the talonavicular joint prosthesis of the present invention.
Figure 8:
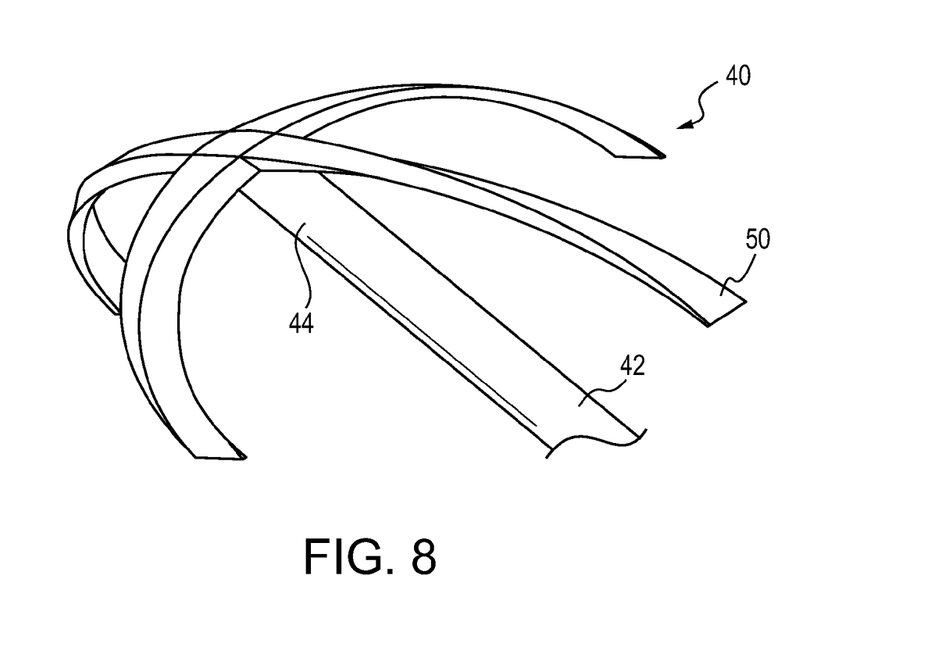
FIG. 8 shows a perspective view of a cutting tool for use in preparing a patient's talus and navicular bones to accommodate said the talonavicular joint prosthesis of the present invention.

For example, a preferred posterior to anterior oriented approach involves the insertion of a guidewire down the long axis of the talus, bisecting the medial and lateral and dorsal and plantar confines of the talar head, neck and body. Over this wire, a path is drilled to introduce a rod within a sheath, which is connected to the present invention's novel cutting tool 40, see FIGS. 7 and 8. In FIG. 7, this cutting tool consists of a rod 42 having an end 44 on which is mounted a head 46 that is generally hemispherically shaped with sharp, cutting facets, edges, protrusions, recessions or perforations 48 that are configured so that the tool has the ability to cut forwards and backwards. It is used to back cut the talar head, making, for example, a spherical relief in anticipation of using a talar component whose inner surface is a portion of a hemispherically shaped cavity so as to generally follow the original anatomic contour of this joint surface while also allowing for the overall thickness of this talar component and the prosthesis to be minimized. It is then used to create a concentric concavity on the navicular in anticipation of using a navicular component whose inner surface is convex with quasi-hemispherical (i.e., it's usually only a portion of a hemisphere) curvature.

Alternative surgical methods of approaching and resecting the talonavicular joint are a medial to lateral, a superior to inferior approach or a combination of such approaches, any of which is perpendicular to the bisecting axis of the talar dome. Appropriate tools may be used to produce flat, curved or beveled cuts. Multiple cuts may be made to estimate a concentric shape, where each cut would be aligned parallel to a cord of the roughly spherical talar dome.

Yet another surgical approach to the necessary joint resection involves the dorsal insertion of a cylindrical guide into the estimated center of the talar dome. This cylinder is then used as a pivot point around which the necessary bone is removed with an appropriate cutting tool. This tool is placed at the end of the radius and swung or shifted from dorsal to plantar. This swinging and cutting action is repeated all along the talar dome surface. This approach produces a cylindrical cut on the talar surface, so that the talar component's inner surface would then have a cylindrical concavity to match the curvature of the talar surface. The talar component's outer surface could have any shape, e.g., such as a portion of a sphere. The navicular joint surface is cut in a similar fashion and the navicular component's inner surface could be shaped cylindrically convex, while its outer surface would be shaped to match the contour of the talar component's outer surface.

Alternatively, the talonavicular joint surface could be replaced in the opposite way while still using this ball and socket type arrangement, but with the inner surface convexity on the navicular side and the concavity on the talus side. All of the surgical approaches described above may be preceded with a combination of distraction and resection processes, including flat cutting, in order to make room for the tools and apparatus necessary to cut the new joint space in the desired way.

All of these alternative surgical approaches, for creating a talonavicular joint space or assisting with the insertion of a guidewire and rod, use a number of different tools either independently or in combination, including a reamer, router, rasp, and flat or crescentic saw. The appropriate cutting tool 40 can have one or more radially oriented cutting blades 50, shaped as slices of a sphere with a sharp cutting edge on the front and/or back side. See FIG. 8. The cutting surfaces of these tools may oscillate, move continuously in one direction or may cover a limited range of back and forth motion. Additionally, appropriate guides will often be necessary for the fixation and placement of the above described cutting tools.

After a new talonavicular joint space is created, there are many different methods and approaches that may be taken for the insertion and attachment of the present invention's components. For example, a preferred way is often to insert the components from the dorsal side. Alternatively, the components may be inserted along other directions, such as medial to lateral, or any direction in between medial to lateral and dorsal to plantar. The components may also be inserted individually or simultaneously. When the components have a single, trapezoidal shaped rail, the rails are generally aligned to accommodate the direction of implant insertion.

To more fully appreciate the design of the present invention, it proves instructive to compare its design to that of the previously discussed joint prosthesis that was disclosed in U.S. Pat. No. 3,965,489. It can be seen that for a preferred embodiment of the present invention, its talar and navicular components have interacting outer surfaces and parallel, concentric inner surfaces so as to allow the distance between each component's outer and inner surfaces to be of a minimal thickness, and with the component's inner surface generally following the anatomic contour of the original joint surface. Since the adjoining bone surfaces do not have to be shaved flat, as they would need to be to accommodate the U.S. Pat. No. 3,965,489 disclosed prosthesis (which also consists of talar and navicular components—but their inner sides are flat surfaces which necessitates the adjoining joint surfaces being shaved flat), bone resorption is reduced and damage to critical bony and soft tissue structures (such as, ligaments, tendons) is minimized, which leads to the expected useful life of the prosthesis being extended. Unlike U.S. Pat. No. 3,965,489, attachment/fixation of the present invention is not dependent on cement or any other gap filling medium alone since it provides for integration of its protrusions into the adjoining bones. Additionally, the design features of the present invention permit the surgeon to correct malalignments, instabilities and structural weaknesses to enhance longevity of the present invention. Known common pathologies that lead to the necessity of these implants (e.g., posterior tibial tendon insufficiency, ligamentous rupture) can now be affectively addressed in conjunction with the implantation of the present invention.

The foregoing is considered as illustrative only of the principles of the invention. Further, since numerous modifications and changes will readily occur to those skilled in the art, and because of the wide extent of the teachings disclosed herein, the foregoing disclosure should not be considered to limit the invention to the exact construction and operation shown and described herein. Accordingly, all suitable modifications and equivalents of the present disclosure may be resorted to and still considered to fall within the scope of the invention as hereinafter set forth in claims to the present invention.

The invention claimed is:

1. A talonavicular joint prosthesis adapted to replace a natural and original talonavicular joint that exists between an anterior-inferior portion of a patient's talus and a superior-posterior portion of said patient's navicular bone after appropriate surgical preparation of said portions of said bones so as to create, with minimal bone resection from said bones, a new joint space to accommodate said prosthesis, said prosthesis comprising:
a talar component having an inner and an outer surface and a herein defined average thickness, $t_T$, that quantifies an average distance between said talar component surfaces, and wherein said talar component surfaces each having a portion that is parallel and concentric to each other so that said talar component average thickness, $t_T$, assumes a minimum value that is consistent with providing sufficient strength and rigidity in said talar component while also providing for said minimal bones resection from said anterior-inferior portion of said talus, said talar component inner surface is further configured to generally follow an anatomic contour of said anterior-inferior portion of said-talus joint surface to which said talar component is to be attached; and
a navicular component having an inner and an outer surface and a herein defined average thickness, $t_N$, that quantifies an average distance between said navicular component surfaces, and wherein said navicular component surfaces each having a portion that is parallel and concentric to each other so that said navicular component average thickness, $t_N$, assumes a minimum value that is consistent with providing sufficient strength and rigidity in said navicular component while also providing for said minimal bones resection from said superior-posterior portion of said navicular bone, said navicular component inner surface is configured to generally follow an anatomic contour of said superior-posterior portion of said navicular joint surface to which said navicular component is to be attached.

2. The talonavicular joint prosthesis as recited in claim 1, further comprising:
a talar protrusion attached to said talar component inner surface and configured to facilitate fixation of said talar component to said talus, and
a navicular protrusion attached to said navicular component inner surface and configured to facilitate fixation of said navicular component to said navicular bone.

3. The talonavicular joint prosthesis as recited in claim 2, wherein:
said talar protrusion having a distal end,
said talonavicular joint prosthesis further comprising a talar implant receptacle configured to be implanted into said anterior-inferior portion of said talus and having an interlocking end that is configured to mate with said talar protrusion distal end.

4. The talonavicular joint prosthesis as recited in claim 2, wherein:
said navicular protrusion having a distal end,
said talonavicular joint prosthesis further comprising a navicular implant receptacle configured to be implanted into said superior-posterior portion of said navicular bone and having an interlocking end that is configured to mate with said navicular protrusion distal end.

5. The talonavicular joint prosthesis as recited in claim 3, wherein:
said navicular protrusion having a distal end,
said talonavicular joint prosthesis further comprising a navicular implant receptacle (38) configured to be implanted into said superior-posterior portion of said navicular bone and having an interlocking end that is configured to mate with said navicular protrusion distal end.

6. The talonavicular joint prosthesis as recited in claim 1, further comprising:
a mobile bearing having a proximal and a distal surface,
said mobile bearing proximal surface configured to adjoin and interact with said talar component outer surface, and
said mobile bearing distal surface configured to adjoin and interact with said navicular component outer surface.

7. The talonavicular joint prosthesis as recited in claim 2, further comprising:
a mobile bearing having a proximal and a distal surface,
said mobile bearing proximal surface configured to adjoin and interact with said talar component outer surface, and
said mobile bearing distal surface configured to adjoin and interact with said navicular component outer surface.

8. The talonavicular joint prosthesis as recited in claim 1, wherein:
said appropriate surgical preparation includes an election of the surgical approach used to access said joint-related portions of said talus and navicular bones, and wherein said surgical approach election is from the group consisting of a posterior to anterior approach, a medial to lateral approach, a superior to inferior approach or a combination of such approaches,
said talar component is further configured according to said surgical approach election made to access said joint-related portions of said talus and navicular bones, and said navicular component is further configured according to said surgical approach election made to access said joint-related portions of said talus and navicular bones.

9. The talonavicular joint prosthesis as recited in claim 2, wherein:
said appropriate surgical preparation includes an election of the surgical approach used to access said joint-related portions of said talus and navicular bones, and wherein said surgical approach election is from the group consisting of a posterior to anterior approach, a medial to lateral approach, a superior to inferior approach or a combination of such approaches,
said talar component is further configured according to said surgical approach election made to access said joint-related portions of said talus and navicular bones, and
said navicular component is further configured according to said surgical approach election made to access said joint-related portions of said talus and navicular bones.

* * * * *